(12) United States Patent
de Villiers et al.

(10) Patent No.: US 9,655,741 B2
(45) Date of Patent: May 23, 2017

(54) PROSTHETIC DISC FOR INTERVERTEBRAL INSERTION

(71) Applicant: Simplify Medical Ptd, Ltd., Paddington (AU)

(72) Inventors: Malan de Villiers, Wapadrand (ZA); Ulrich Hahnle, Saxonwold (ZA)

(73) Assignee: Simplify Medical PTY LTD (AU)

( * ) Notice: Subject to any disclaimer, the term of this patent is extended or adjusted under 35 U.S.C. 154(b) by 0 days.

(21) Appl. No.: 15/151,310

(22) Filed: May 10, 2016

(65) Prior Publication Data

US 2016/0250035 A1 Sep. 1, 2016

Related U.S. Application Data

(63) Continuation of application No. 14/612,431, filed on Feb. 3, 2015, which is a continuation of application
(Continued)

(51) Int. Cl.
*A61F 2/44* (2006.01)
*A61F 2/50* (2006.01)
*A61F 2/30* (2006.01)

(52) U.S. Cl.
CPC ............ *A61F 2/4425* (2013.01); *A61F 2/442* (2013.01); *A61F 2002/3008* (2013.01); *A61F 2002/30131* (2013.01); *A61F 2002/30245* (2013.01); *A61F 2002/30299* (2013.01); *A61F 2002/30518* (2013.01); *A61F 2002/30649* (2013.01);
(Continued)

(58) Field of Classification Search
CPC ... A61F 2/4425; A61F 2002/443; A61F 2/447
See application file for complete search history.

(56) References Cited

U.S. PATENT DOCUMENTS 3,486,505 A 12/1969 Gordon
3,867,728 A 2/1975 Stubstad et al.
(Continued)

FOREIGN PATENT DOCUMENTS

DE 3023353 A1 4/1981
DE 10035182 A1 2/2002
(Continued)

OTHER PUBLICATIONS

Buttner-Janz, The Development of the Artificial Disc. Introduction, pp. 1-18, Library of Congress Catalogue No. 92-75582, ISBN 0-9635430-0-8 (1989).
(Continued)

*Primary Examiner* — Anu Ramana
(74) *Attorney, Agent, or Firm* — Wilson Sonsini Goodrich & Rosati

(57) ABSTRACT

A prosthetic disc for insertion between adjacent vertebrae includes a core having upper and lower curved surfaces, upper and lower plates, and peripheral restraining structure on at least one of the upper plate, the lower plate and the core. Each plate has an outer surface which engages a vertebra and an inner curved surface which slides over the curved surface of the core. The peripheral restraining structure serves to hold the core against a curved surface of at least one of the plates during sliding movement of the plates over the core.

10 Claims, 3 Drawing Sheets

Related U.S. Application Data

No. 14/150,437, filed on Jan. 8, 2014, now Pat. No. 8,974,533, which is a continuation of application No. 12/626,027, filed on Nov. 25, 2009, now Pat. No. 8,845,729, which is a continuation of application No. 10/855,253, filed on May 26, 2004, now Pat. No. 7,753,956.

(60) Provisional application No. 60/473,802, filed on May 27, 2003, provisional application No. 60/473,803, filed on May 27, 2003.

(52) U.S. Cl.
CPC .......... *A61F 2002/30785* (2013.01); *A61F 2002/30822* (2013.01); *A61F 2002/30838* (2013.01); *A61F 2002/30884* (2013.01); *A61F 2002/30904* (2013.01); *A61F 2002/443* (2013.01); *A61F 2002/5098* (2013.01); *A61F 2230/0076* (2013.01); *A61F 2310/00179* (2013.01)

(56) References Cited

U.S. PATENT DOCUMENTS

| | | |
|---|---|---|
| 4,309,777 A | 1/1982 | Patil |
| 4,531,917 A | 7/1985 | Linkow et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buettner-Janz et al. |
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,314,477 A | 5/1994 | Marnay |
| 5,320,644 A | 6/1994 | Baumgartner |
| 5,370,697 A | 12/1994 | Baumgartner |
| 5,394,457 A | 2/1995 | Leibinger et al. |
| 5,401,269 A | 3/1995 | Buettner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Büttner-Janz |
| 5,562,738 A | 10/1996 | Boyd et al. |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,836,948 A | 11/1998 | Zucherman et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schaer et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zucherman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,579,320 B1 | 6/2003 | Gauchet et al. |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer et al. |

(56) References Cited

U.S. PATENT DOCUMENTS

| | | |
|---|---|---|
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,755,841 B2 | 6/2004 | Fraser et al. |
| 6,764,512 B2 | 7/2004 | Keller |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthen |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,583 B1 | 12/2007 | Schaer et al. |
| 7,318,839 B2 | 1/2008 | Malberg, I et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | De Villiers et al. |
| 7,452,380 B2 | 11/2008 | Zubok et al. |
| 7,491,241 B2 | 2/2009 | Errico et al. |
| 7,494,508 B2 | 2/2009 | Zeegers et al. |
| 7,517,363 B2* | 4/2009 | Rogers ............... A61F 2/4425 623/17.11 |
| 7,531,001 B2 | 5/2009 | De Villiers et al. |
| 7,585,326 B2 | 9/2009 | De Villiers et al. |
| 7,637,913 B2 | 12/2009 | De Villiers et al. |
| 7,682,396 B2 | 3/2010 | Beaurain et al. |
| 7,753,956 B2 | 7/2010 | De Villiers et al. |
| 7,862,614 B2 | 1/2011 | Keller et al. |
| 8,062,371 B2 | 11/2011 | De Villiers et al. |
| 8,444,695 B2 | 5/2013 | De Villiers et al. |
| 8,454,698 B2 | 6/2013 | De Villiers et al. |
| 8,845,729 B2 | 9/2014 | De Villiers et al. |
| 8,974,533 B2 | 3/2015 | De Villiers et al. |
| 2001/0016773 A1 | 8/2001 | Serhan et al. |
| 2001/0029377 A1 | 10/2001 | Aebi et al. |
| 2001/0056302 A1 | 12/2001 | Boyer et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree et al. |
| 2003/0083747 A1 | 5/2003 | Winterbottom et al. |
| 2003/0100951 A1 | 5/2003 | Serhan et al. |
| 2003/0125739 A1 | 7/2003 | Bagga et al. |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2003/0233155 A1 | 12/2003 | Slemmer et al. |
| 2004/0002761 A1 | 1/2004 | Rogers et al. |
| 2004/0024407 A1 | 2/2004 | Ralph et al. |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0138749 A1 | 7/2004 | Zucherman et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |

(56) References Cited

U.S. PATENT DOCUMENTS

| | | |
|---|---|---|
| 2005/0021145 A1 | 1/2005 | De Villiers et al. |
| 2005/0021146 A1 | 1/2005 | De Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg et al. |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0216081 A1 | 9/2005 | Taylor et al. |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0251262 A1 | 11/2005 | De Villiers et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish, Jr. et al. |
| 2006/0015183 A1 | 1/2006 | Gilbert et al. |
| 2006/0020342 A1 | 1/2006 | Ferree et al. |
| 2006/0025862 A1 | 2/2006 | Villiers et al. |
| 2006/0029186 A1 | 2/2006 | De Villiers et al. |
| 2006/0030857 A1 | 2/2006 | De Villiers et al. |
| 2006/0030862 A1 | 2/2006 | De Villiers et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Ferree |
| 2006/0069439 A1 | 3/2006 | Zucherman et al. |
| 2006/0142858 A1 | 6/2006 | Colleran et al. |
| 2006/0142862 A1 | 6/2006 | Diaz et al. |
| 2006/0155378 A1 | 7/2006 | Eckman |
| 2006/0167549 A1 | 7/2006 | Mathys, Jr. et al. |
| 2006/0178744 A1 | 8/2006 | De Villiers et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0293752 A1 | 12/2006 | Moumene et al. |
| 2006/0293754 A1 | 12/2006 | Devilliers et al. |
| 2007/0010826 A1 | 1/2007 | Rhoda et al. |
| 2007/0021837 A1 | 1/2007 | Ashman |
| 2007/0032875 A1 | 2/2007 | Blacklock et al. |
| 2007/0061011 A1 | 3/2007 | De Villiers et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0088440 A1 | 4/2007 | Eisermann et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0282449 A1 | 12/2007 | De Villiers et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | De Villiers et al. |
| 2008/0051901 A1 | 2/2008 | De Villiers et al. |
| 2008/0125864 A1 | 5/2008 | De Villiers et al. |
| 2008/0133011 A1 | 6/2008 | De Villiers et al. |
| 2008/0154301 A1 | 6/2008 | De Villiers et al. |
| 2008/0154382 A1 | 6/2008 | De Villiers et al. |
| 2008/0215155 A1 | 9/2008 | De Villiers et al. |
| 2008/0221696 A1 | 9/2008 | De Villiers et al. |
| 2008/0228274 A1 | 9/2008 | De Villiers et al. |
| 2008/0228277 A1 | 9/2008 | De Villiers et al. |
| 2008/0294259 A1 | 11/2008 | De Villiers et al. |
| 2009/0043391 A1 | 2/2009 | De Villiers et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0222101 A1 | 9/2009 | De Villiers et al. |
| 2009/0276051 A1 | 11/2009 | Arramon et al. |
| 2010/0004746 A1 | 1/2010 | Arramon |
| 2010/0016972 A1 | 1/2010 | Jansen et al. |
| 2010/0016973 A1 | 1/2010 | De Villiers et al. |
| 2010/0049040 A1 | 2/2010 | De Villiers et al. |
| 2010/0069976 A1 | 3/2010 | De Villiers et al. |
| 2010/0076558 A1 | 3/2010 | De Villiers et al. |
| 2010/0191338 A1 | 7/2010 | De Villiers et al. |
| 2014/0128976 A1 | 5/2014 | De Villiers et al. |

FOREIGN PATENT DOCUMENTS

| | | |
|---|---|---|
| EP | 0333990 A2 | 9/1989 |
| EP | 0333990 A3 | 5/1990 |
| EP | 0560140 A1 | 9/1993 |
| EP | 0560141 A1 | 9/1993 |
| EP | 0591712 A1 | 4/1994 |
| EP | 0820740 A1 | 1/1998 |
| EP | 1142544 A1 | 10/2001 |
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1405615 A1 | 4/2004 |
| EP | 1417940 A1 | 5/2004 |
| EP | 1570813 A1 | 9/2005 |
| FR | 2803741 A1 | 7/2001 |
| JP | S61122859 A | 6/1986 |
| JP | S63164948 A | 7/1988 |
| JP | H01136655 A | 5/1989 |
| JP | H067391 A | 1/1994 |
| JP | 2002521090 A | 7/2002 |
| JP | 2003508119 A | 3/2003 |
| WO | WO-9920209 A1 | 4/1999 |
| WO | WO-9930651 A1 | 6/1999 |
| WO | WO-0004851 A1 | 2/2000 |
| WO | WO-0035384 A1 | 6/2000 |
| WO | WO-0042954 A2 | 7/2000 |
| WO | WO-0042954 A3 | 11/2000 |
| WO | WO-0101893 A1 | 1/2001 |
| WO | WO-0115637 A1 | 3/2001 |
| WO | WO-0168003 A1 | 9/2001 |
| WO | WO-0211650 A2 | 2/2002 |
| WO | WO-04000170 A1 | 12/2003 |

(56) References Cited

FOREIGN PATENT DOCUMENTS

| | | |
|---|---|---|
| WO | WO-04000171 A1 | 12/2003 |
| WO | WO-2004026187 A1 | 4/2004 |
| WO | WO-2004054477 A1 | 7/2004 |
| WO | WO-2005004756 A2 | 1/2005 |
| WO | WO-2005004756 A3 | 5/2005 |
| WO | WO-2005053580 A1 | 6/2005 |
| WO | WO-2005072662 A1 | 8/2005 |
| WO | WO-2005112834 A2 | 12/2005 |
| WO | WO-2005112834 A3 | 5/2006 |
| WO | WO-2006119092 A2 | 11/2006 |
| WO | WO-2006119092 A3 | 12/2006 |
| WO | WO-2007121320 A2 | 10/2007 |
| WO | WO-2007121320 A3 | 6/2008 |
| ZA | 20039312 | 11/2003 |

OTHER PUBLICATIONS

Hellier, et al., Wear Studies for Development of an Intervertebral Disc Prosthesis. Spine, vol. 17 No. 6 Supplement pp. 86-96 (1992).
International search report dated Jul. 21, 2005 for PCT/US2005/026160.
International search report dated Jul. 27, 2007 for PCT/US2006/002263.
Japanese office action dated Jun. 22, 2009 for JP 2006-533469.
Lee, et al. Impact Response of the Intervertebral Disc in a Finite-Element Model. Spine. 2000; 25(19):2431-2439.
Lehuec, et al. Shock Absorption in Lumber Disc Prosthesis. Journal of Spinal Disorders & Techniques. 2003; 16(4):346-351.
Notice of allowance dated Mar. 20, 2013 for U.S. Appl. No. 12/030,772.
Notice of allowance dated Mar. 21, 2013 for U.S. Appl. No. 12/464,670.
Notice of allowance dated Mar. 22, 2010 for U.S. Appl. No. 10/855,253.
Notice of allowance dated Jun. 10, 2014 for U.S. Appl. No. 12/626,027.
Notice of allowance dated Nov. 21, 2014 for U.S. Appl. No. 14/150,437.
Office action dated Mar. 21, 2014 for U.S. Appl. No. 12/626,027.
Office action dated Apr. 4, 2007 for U.S. Appl. No. 10/855,253.
Office action dated Apr. 4, 2012 for U.S. Appl. No. 12/464,670.
Office action dated Apr. 23, 2014 for U.S. Appl. No. 14/150,437.
Office action dated May 7, 2012 for U.S. Appl. No. 12/030,772.
Office action dated Jun. 12, 2008 for U.S. Appl. No. 10/855,253.
Office action dated Jul. 16, 2009 for U.S. Appl. No. 10/855,253.
Office action dated Jul. 17, 2012 for U.S. Appl. No. 12/626,027.
Office action dated Sep. 1, 2011 for U.S. Appl. No. 12/464,670.
Office action dated Sep. 12, 2014 for U.S. Appl. No. 14/150,437.
Office action dated Sep. 13, 2013 for U.S. Appl. No. 12/626,027.
Office action dated Sep. 26, 2011 for U.S. Appl. No. 12/030,772.
Office action dated Oct. 28, 2009 for U.S. Appl. No. 10/855,253.
Office action dated Nov. 19, 2012 for U.S. Appl. No. 12/030,772.
Office action dated Nov. 24, 2008 for U.S. Appl. No. 10/855,253.
Office action dated Dec. 9, 2011 for U.S. Appl. No. 12/626,027.
Office action dated Dec. 14, 2012 for U.S. Appl. No. 12/464,670.
Office action dated Dec. 14, 2012 for U.S. Appl. No. 12/626,027.
U.S. Appl. No. 14/612,431, filed Feb. 3, 2015.

* cited by examiner

PROSTHETIC DISC FOR INTERVERTEBRAL INSERTION

CROSS-REFERENCE TO RELATED APPLICATION

The present application is a continuation of U.S. patent application Ser. No. 14/612,431, filed Feb. 3, 2015, which is a continuation of U.S. patent application Ser. No. 14/150,437, filed Jan. 8, 2014 (now U.S. Pat. No. 8,974,533), which is continuation of U.S. patent application Ser. No. 12/626,027, filed Nov. 25, 2009, (now U.S. Pat. No. 8,845,729), which is a continuation of U.S. patent application Ser. No. 10/855,253, filed May 26, 2004, (now U.S. Pat. No. 7,753,956), which application claims the benefit of U.S. Provisional Application No. 60/473,802 and 60/473,803, both filed May 27, 2003; all of which are incorporated herein by reference in their entirety.

BACKGROUND OF THE INVENTION

1. Field of the Invention

This invention relates to medical devices and methods. More specifically, the invention relates to a prosthetic disc for intervertebral insertion, such as in the lumbar and cervical spine.

In the event of damage to a lumbar or cervical intervertebral disc, one possible surgical treatment is to replace the damaged disc with a disc prosthesis. Several types of intervertebral disc prostheses are currently available. For example, one type of intervertebral disc prosthesis is provided by Waldemar Link GmbH & Co under the trademark LINK SB CHARITE™. This prosthesis includes upper and lower prosthesis plates or shells which locate against and engage the adjacent vertebral bodies, and a low friction core between the plates. The core has upper and lower convexly curved surfaces and the plates have corresponding, concavely curved recesses which cooperate with the curved surfaces of the core. This allows the plates to slide over the core to allow required spinal movements to take place. The curved recesses in the plates are surrounded by annular ridges which locate, at the limit of sliding movement of the plates over the core, in opposing upwardly and downwardly facing, peripheral channels surrounding the curved surfaces of the core.

This type of disc configuration is described in EP 1142544A1 and EP 1250898A1, assigned to Waldemar Link GmbH & Co. A drawback of such configurations is that the provision of the peripheral ribs and channels limits the areas available for bearing and sliding contact between the plates and core, and accordingly the loads which can be transmitted by the prosthesis. As a result of the relatively small bearing areas, it is believed that at least the core will be subject to rapid wear and have a relatively short lifespan. Also, because the core is in effect merely "clamped" between the plates, this configuration does not allow for secure retention of the core. In one alternative arrangement, the curved surfaces of the core carry opposing, elongate keys that locate in elongate grooves in the plates and another alternative arrangement in which the plates have opposing elongate keys that locate in elongate grooves in the opposite curved surfaces of the core. These key and groove arrangements allow the plates to slide over the core within the limits of the length of the grooves, in one direction only. Although allowance is made for some lateral play of the keys in the grooves, very little sliding movement of the plates over the core can take place in the orthogonal vertical plane, and this is considered to be a serious drawback of this design.

Other currently available intervertebral disc prostheses have similar and/or other drawbacks. Typically, drawbacks include insufficient resistance to wear and tear, restricted range of motion and/or insufficient ability of the prosthesis to adhere to vertebral bone.

Therefore, a need exists for improved intervertebral disc prostheses. Ideally, such improved prostheses would resist wear and tear, provide a desired range of motion and adhere well to vertebral bone. At least some of these objectives will be met by the present invention.

2. Description of the Background Art

Published US patent applications 2002/0035400A1 and 2002/0128715A1 describe disc implants which comprise opposing plates with a core between them over which the plates can slide. The core receives one or more central posts, which are carried by the plates and which locate in opposite ends of a central opening in the core. Such arrangements limit the load bearing area available between the plates and core.

Other patents related to intervertebral disc prostheses include U.S. Pat. Nos. 4,759,766; 4,863,477; 4,997,432; 5,035,716; 5,071,437; 5,370,697; 5,401,269; 5,507,816; 5,534,030; 5,556,431; 5,674,296; 5,676,702; 5,702,450; 5,824,094; 5,865,846; 5,989,291; 6,001,130; 6,022,376; 6,039,763; 6,139,579; 6,156,067; 6,162,252; 6,315,797; 6,348,071; 6,368,350; 6,416,551; 6,592,624; 6,607,558 and 6,706,068. Other patent applications related to intervertebral disc prostheses include U.S. Patent Application Publication Nos.: 2003/0009224; 2003/0074076; 2003/0191536; 2003/0208271; 2003/0135277; 2003/0199982; 2001/0016773 and 2003/0100951. Other related patents include WO 01/01893A1, EP 1344507, EP 1344506, EP 1250898, EP 1306064, EP 1344508, EP 1344493, EP 1417940, EP 1142544, and EP 0333990.

BRIEF SUMMARY OF THE INVENTION

In one aspect of the present invention, a prosthetic disc for insertion between adjacent vertebrae includes upper and lower plates having outer surfaces, which engage and are locatable against the respective vertebrae, and inner curved surfaces. A core is disposed between the curved surfaces to allow the plates to slide over the core. Preferably, the plates can slide freely in all directions, not being limited to movement in a single direction as with the prior art. The present invention further provides peripheral restraining structure on one or both of the plates or the core to hold the core against the curved surface of at least one of the plates during sliding movement of the plates over the core. The peripheral restraining structure defines a limit or boundary for movement of the core relative to at least one of the upper and lower plates. Within such a peripheral boundary, however, movement of the core relative to the plate will preferably be unconstrained. That is, movement of the core relative to the plate may occur in any direction without significant inhibition or friction. The core will preferably not be attached to either the upper or lower plate, and the plates will thus be able to freely articulate relative to each other over the core, which provides a low friction bearing surface.

An advantage of the structure thus described is that the surface contact area between the core and each of the upper and lower plates may be maximized. By providing only a peripheral restraint, as opposed for example to grooves and keys on the surface of the core and plates, the width or diameter of the core relative to the size of the plate may be maximized. Moreover, the surfaces of the core and the plates which contact each other may be made smooth and free from other structure(s) that might adversely affect performance. In the preferred embodiments, both the curved surfaces of the plates and the corresponding surfaces of the core will be spherical sections. The use of spherical surfaces promotes free, unconstrained relative motion of the plates and the core in all directions.

In some embodiments, the peripheral restraining structure limits relative inclination of the plates during sliding movement of the plates over the core, usually by defining a stop structure. In other embodiments, the peripheral restraining structure lifts one side of the core relative to an opposite side of the core during sliding movement of the plates over the core. The peripheral restraining structure itself may take any of a number of different forms. In one embodiment, for example, the restraining structure comprises a ring structure on at least one of the upper and lower plates and an annular structure on at least a portion of the periphery of the core. The ring structure will be adapted to engage and restrain the annular structure on the core. For example, the ring structure may comprise a flange which defines an overhang over at least a portion of the periphery of one of the plates. The overhang of the flange will receive the annular structure on the core to provide an interference fit which retains the core against the curved surface of the plate but allows the core to slide freely and in an unconstrained manner within the limit or boundary defined by the flange. The annular structure on the core may be a rim which extends continuously or discontinuously (preferably continuously) around a lateral circumference of the core. By providing a rim which has a width, usually a diameter, which is slightly greater than the corresponding width of an inner edge of the flange at one point, the core will be held in place and will not be dislodged from the cavity defined by the ring structure in normal use.

Usually, the flange or other ring structure as well as the rim or other annular structure will be formed continuously about the periphery of the plate and core, respectively. Alternatively, however, either or both of the annular structure and the ring structure could be formed discontinuously. That is, so long as at least some portion of the ring structure and the annular structure remain engaged during all expected geometries and uses of the prosthetic disc, the objective of holding the core against the curved surface of the plate will be met.

The upper and lower plates may be made of any suitable material or combination of materials, such as but not limited to cobalt chrome molybdenum and titanium. In some embodiments, titanium plates are used, and these plates may optionally include inner surfaces of titanium nitride and outer surfaces that are aluminum oxide blasted to create micro-concavities. In another embodiment, cobalt chrome plates are used, with the outer surfaces being blasted with aluminum oxide and then coated with a titanium plasma spray. In some embodiments, the plates comprise an MRI-compatible material, such as titanium, coupled with a hardened material, such as cobalt chrome molybdenum. Such materials may be coupled using any suitable means, such as laminating, slip fitting, interferences fitting, adhesion, welding, molding or the like. Some plates include a coating or material on the inner surfaces for reducing friction and/or wear and tear, such as a titanium nitride surface.

Optionally, in some embodiments the outer surfaces of the upper and lower plates have at least one surface feature for promoting attachment of the outer surfaces to the vertebrae. For example, such surface features may include a plurality of serrations disposed along the outer surfaces. Some embodiments include additional or alternative features on the outer surfaces for enhancing attachment of the prosthesis to vertebral bone, such as a material or coating, like a titanium plasma spray. Multiple micro-concavities may be formed on the outer surfaces, for example by aluminum oxide spraying, to further enhance attachment. Additionally or alternatively, the surface features may include at least one fin disposed on each of the outer surfaces. In some embodiments, the fin includes at least one hole for further promoting attachment to the vertebrae. Fins may extend vertically from their corresponding outer surfaces at right angles, or alternatively the fins may extend from their corresponding outer surface at angles other than 90°. Fins may also have any suitable orientation relative to the anterior-posterior axis of the prosthesis. For example, a fin may extend in a straight line from anterior to posterior, without being angled. Alternatively, the fin may be rotated or angled away from the anterior-posterior axis at any suitable angle between 0° and 180°. In one embodiment, each fin is disposed in a lateral orientation on the outer surfaces.

The core may generally have any suitable configuration and be made of any suitable material or combination of materials, such as polymers, ceramics or the like. In some embodiments, the core comprises a low-friction material and has two convex surfaces for slidably engaging the inner, curved surfaces of the upper and lower plates.

In another aspect of the present invention, a prosthetic disc for insertion between adjacent vertebrae includes upper and lower plates and a free-floating core disposed between the plates. Again, the upper and lower plates have outer surfaces locatable against the respective vertebrae and inner, curved surfaces. Additionally, at least one of the upper and lower plates includes a flange extending from one of the inner surfaces. The core includes at least one peripheral groove for engaging with the flange(s) to hold the core captive between the plates during sliding movement of the plates over the core. Any of the features described above may also be incorporated in various embodiments.

In another aspect of the present invention, a prosthetic disc for insertion between adjacent vertebrae includes upper and lower plates having outer surfaces locatable against the respective vertebrae and inner, curved surfaces, at least one of the upper and lower plates including a flange extending from one of the inner surfaces. A free-floating core is disposed between the curved surfaces to allow the plates to slide over the core, and the core includes at least one peripheral protrusion for engaging with the flange(s) to hold the core captive between the plates during sliding movement of the plates over the core. Again, various embodiments may include any of the features described above.

In yet another aspect of the invention, a prosthetic disc for insertion between adjacent vertebrae includes upper and lower plates having outer surfaces locatable against the respective vertebrae and inner curved surfaces, a core between the plates, and opposing retaining formations. The core includes upper and lower curved surfaces complementary in shape to the inner, curved surfaces of the plates to allow the plates to slide over the core, the upper and lower surfaces of the core being located respectively above and below an equatorial plane extending laterally through the core. The opposing retaining formations are located peripherally on the equatorial plane of the core and at an edge of the curved surface of at least one of the plates and serve to hold the core captive between the plates during sliding movement of the plates over the core.

In yet another aspect of the invention, a method for restraining spacing between adjacent vertebrae involves implanting an upper plate against a lower surface of an upper vertebral body, implanting a lower plate against an upper surface of a lower vertebral body, and disposing a core between the upper and lower plates The core floats between spherical cavities in each of the upper and lower plates, the plates restraining peripheral movement of the core using at least one peripheral restraining member. In some embodiments, implanting each of the plates comprises sliding a fin on each plate into a corresponding groove formed in its respective vertebral body. The fin may slide into the groove in any suitable direction, such as posterior-anterior, anterior-posterior, lateral, or any angled direction between an anterior-posterior orientation and a lateral orientation. Optionally, implanting may further involve contacting textured outer surfaces of the upper and lower plates with the upper and lower surfaces of the vertebral bodies.

In another aspect of the invention, a method for assembling a prosthetic disc for insertion between adjacent vertebrae involves movably coupling a core with a first endplate to form an interference fit between the core and the first endplate and contacting the core with a second endplate. In some embodiments, coupling the core with the first endplate comprises snap fitting the core into the endplate. Alternatively, coupling the core with the first endplate may comprise forming the endplate around the core. In some embodiments, coupling the core with the first endplate involves engaging a peripheral protrusion of the core with a peripheral restraining structure of the first endplate.

These and other aspects and embodiments will be described in further detail below, with reference to the drawing figures.

DETAILED DESCRIPTION OF THE INVENTION

Figure 1:
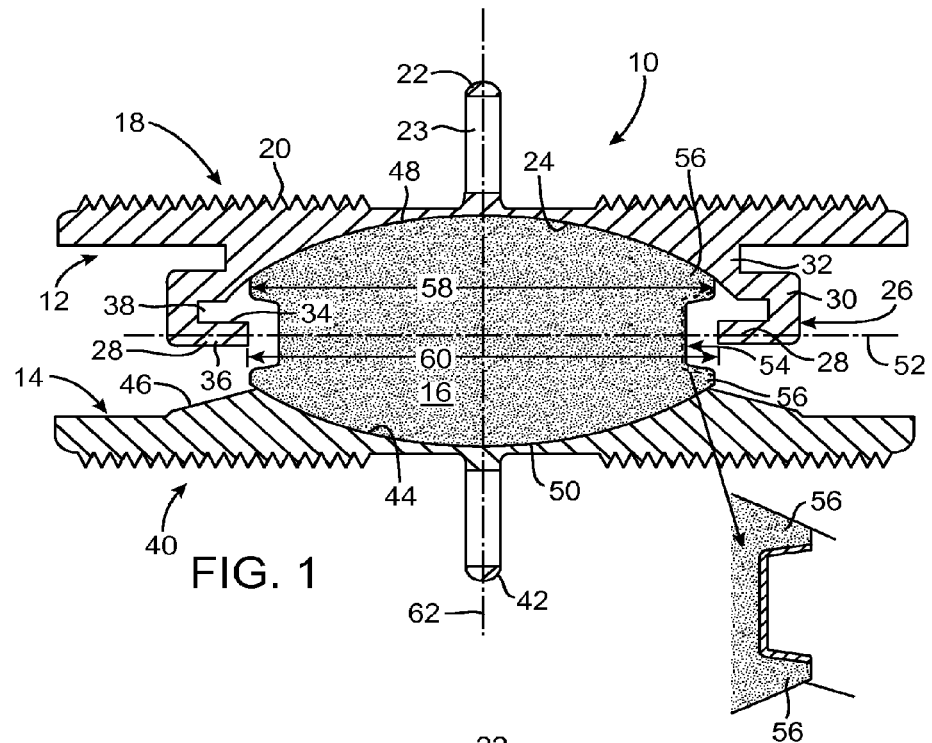
FIG. 1 shows a cross-sectional anterior view of a prosthetic disc with the prosthesis plates and core in vertical alignment, according to one embodiment of the present invention.

FIGS. 1 to 4 illustrate a prosthetic disc 10 for intervertebral insertion between two adjacent spinal vertebrae (not shown). The disc 10 comprises three components, namely an upper plate or shell 12, a lower plate or shell 14 and a core 16 located between the plates.

The upper plate 12 includes an outer surface 18 and an inner surface 24 and may be constructed from any suitable material or combination of materials, such as but not limited to cobalt chrome molybdenum, titanium (such as grade 5 titanium) and/or the like. In one embodiment, typically used in the lumbar spine, the upper plate 12 is constructed of cobalt chrome molybdenum, and the outer surface 18 is treated with aluminum oxide blasting followed by a titanium plasma spray. In another embodiment, typically used in the cervical spine, the upper plate 12 is constructed of titanium, the inner surface 24 is coated with titanium nitride, and the outer surface 18 is treated with aluminum oxide blasting. An alternative cervical spine embodiment includes no coating on the inner surface 24. In some embodiments, it may be useful to couple two materials together to form the inner surface 24 and the outer surface 18. For example, the upper plate 12 may be made of an MRI-compatible material, such as titanium, but may include a harder material, such as cobalt chrome molybdenum, for the inner surface 24. Any suitable technique may be used to couple materials together, such as snap fitting, slip fitting, lamination, interference fitting, use of adhesives, welding and/or the like. Any other suitable combination of materials and coatings may be employed in various embodiments of the invention.

Figure 6:
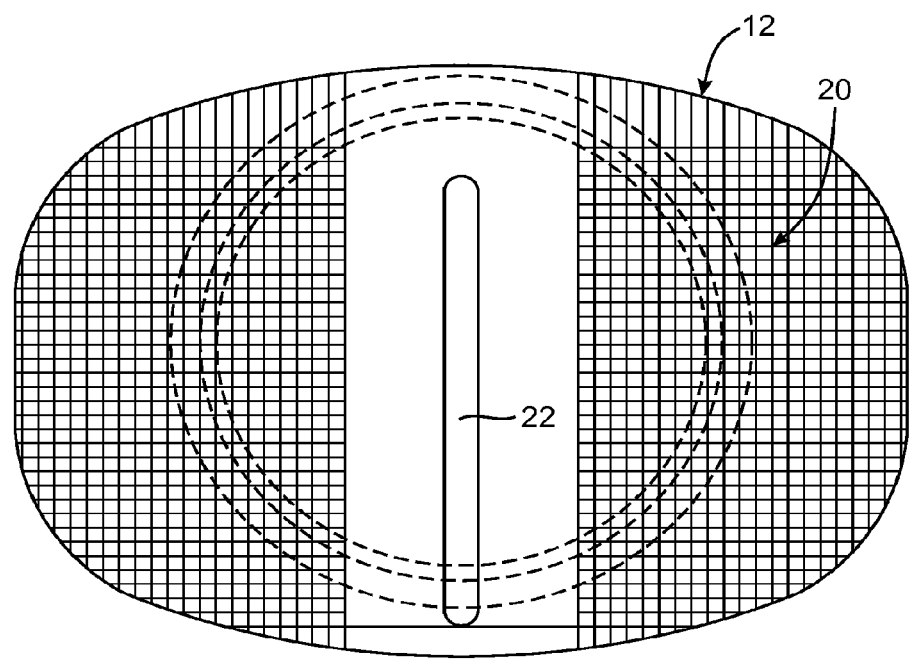
FIG. 6 shows a plan view of an upper plate of a prosthetic disc, according to one embodiment of the present invention.

In some embodiments, the outer surface 18 is planar. Oftentimes, the outer surface 18 will include one or more surface features and/or materials to enhance attachment of the prosthesis 10 to vertebral bone. For example, the outer surface 18 may be machined to have a serrations 20 or other surface features for promoting adhesion of the upper plate 12 to a vertebra. In the embodiment shown (FIG. 6), the serrations 20 extend in mutually orthogonal directions, but other geometries would also be useful. Additionally, the outer surface 18 may be provided with a rough microfinish formed by blasting with aluminum oxide microparticles or the like. In some embodiments, the outer surface may also be titanium plasma sprayed to further enhance attachment of the outer surface 18 to vertebral bone.

The outer surface 18 may also carry an upstanding, vertical fin 22 extending in an anterior-posterior direction. The fin 22 is pierced by transverse holes 23. In alternative embodiments, the fin 22 may be rotated away from the anterior-posterior axis, such as in a lateral-lateral orientation, a posterolateral-anterolateral orientation, or the like. In some embodiments, the fin 22 may extend from the surface 18 at an angle other than 90°. Furthermore, multiple fins 22 may be attached to the surface 18 and/or the fin 22 may have any other suitable configuration, in various embodiments. In other embodiments, the fin 22 In some embodiments, such as discs 10 for cervical insertion, the fins 22, 42 may be omitted altogether.

The inner, spherically curved concave surface 24 is formed at a central, axial position with a circular recess 26 as illustrated. At the outer edge of the curved surface 24, the upper plate 12 carries peripheral restraining structure comprising an integral ring structure 26 including an inwardly directed rib or flange 28. The flange 28 forms part of a U-shaped member 30 joined to the major part of the plate by an annular web 32. The flange 28 has an inwardly tapering shape and defines upper and lower surfaces 34 and 36 respectively which are inclined slightly relative to the horizontal when the upper plate 12 is at the orientation seen in FIG. 1. An overhang 38 of the U-shaped member 30 has a vertical dimension that tapers inwardly as illustrated.

The lower plate 14 is similar to the upper plate 12 except for the absence of the peripheral restraining structure 26. Thus, the lower plate 14 has an outer surface 40 which is planar, serrated and microfinished like the outer surface 18 of the upper plate 12. The lower plate 14 optionally carries a fin 42 similar to the fin 22 of the upper plate. The inner surface 44 of the lower plate 14 is concavely, spherically curved with a radius of curvature matching that of the inner surface 24 of the upper plate 12. Once again, this surface may be provided with a titanium nitride or other finish.

At the outer edge of the inner curved surface 44, the lower plate 14 is provided with an inclined ledge formation 46.

Alternatively, the lower plate 14 may include peripheral restraining structure analogous to the peripheral restraining structure 26 on the upper plate 12.

The core 16 of the disc 10 is made of a low-friction material, such as polyethylene (Chirulen™). In alternative embodiments, the core 16 may comprise any other suitable material, such as other polymers, ceramics or the like. The core 16 has identical upper and lower spherically curved convex surfaces 48, 50. The radius of curvature of these surfaces matches the radius of curvature of the inner surfaces 24, 44 of the upper and lower plates 12, 14. The curved surfaces are accordingly complementary. For wear resistance, the surface zones of the core may be hardened by an appropriate cross-linking procedure.

The core 16 is symmetrical about a central, equatorial plane 52 which bisects it laterally. (Although in other embodiments, the core 16 may be asymmetrical.) Lying on this equatorial plane is an annular recess or groove 54 which extends about the periphery of the core. The groove 54 is defined between upper and lower ribs or lips 56. When the plates 12, 14 and core 16 are assembled and in the orientation seen in FIG. 1, the flange 28 lies on the equatorial plane and directly aligned with the groove 54. The outer diameter 58 of the lips 56 is preferably very slightly larger than the diameter 60 defined by the inner edge of the flange 28. Assembly of the core and upper plate may involve pressing the core through the circular aperture defined by the flange 28, with the inherent resilience of the core allowing the minor deformation of the upper rib 56, or that the core be introduced at an inclination. In other less preferred embodiments of the invention (not shown), the diameter 58 may be equal to or even slightly less than the diameter 60.

In some embodiments, the inner surface of the groove 54 may be provided, for wear resistance, with a lining of pure titanium or titanium impregnated with cobalt chrome, titanium nitride, other titanium alloy or the like.

Figure 4:
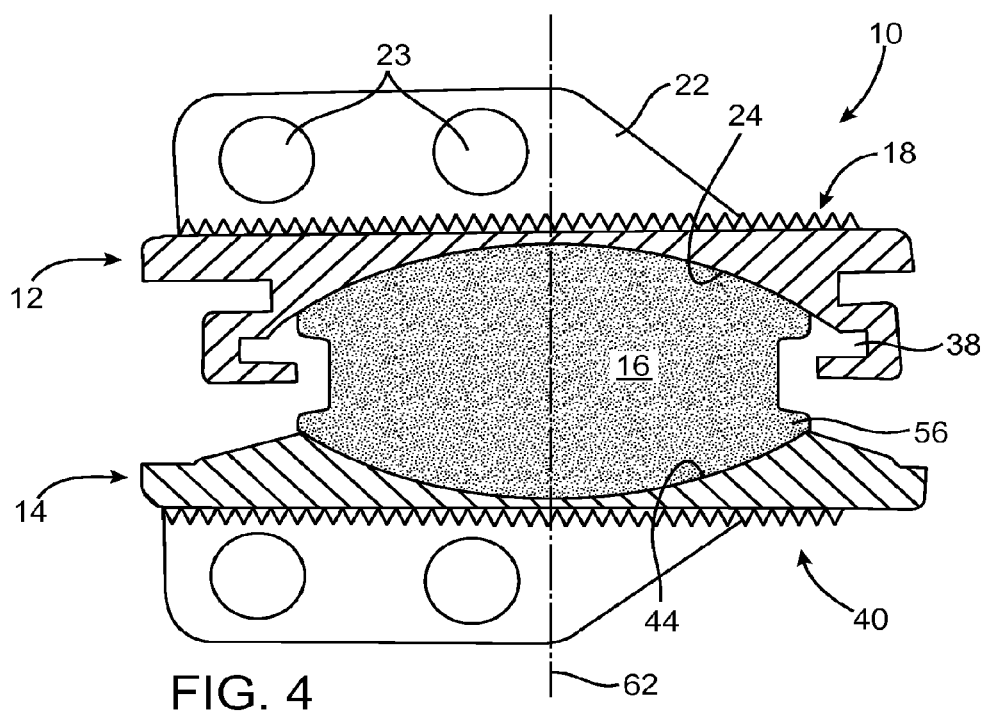
FIG. 4 shows a side view of the prosthetic disc in FIG. 1 with the prosthesis plates and core in vertical alignment.

The central axis of the disc 10 (the axis passing through the centers of curvature of the curved surfaces) is indicated with the reference numeral 62. As shown in FIG. 1, the disc 10 may be symmetrical about a central anterior-posterior plane containing the axis 62. Referring to FIG. 4, in some embodiments the axis 62 is posteriorly disposed, i.e. is located closer to the posterior limit of the disc than the anterior limit thereof.

In use, the disc 10 is surgically implanted between adjacent spinal vertebrae in place of a damaged disc. The adjacent vertebrae are forcibly separated from one another to provide the necessary space for insertion. The disc is inserted, normally in a posterior direction, into place between the vertebrae with the fins 22, 42 of the plates 12, 14 entering slots cut in the opposing vertebral surfaces to receive them. After insertion, the vertebrae, facets, adjacent ligaments and soft tissues are allowed to move together to hold the disc in place. The serrated and microfinished surfaces 18, 40 of the plates 12, 14 locate against the opposing vertebrae. The serrations 20 and fins 22, 42 provide initial stability and fixation for the disc 10. With passage of time, enhanced by the titanium surface coating, firm connection between the plates and the vertebrae will be achieved as bone tissue grows over the serrated surface. Bone tissue growth will also take place about the fins 22, 40 and through the transverse holes 23 therein, further enhancing the connection which is achieved.

Figure 5:
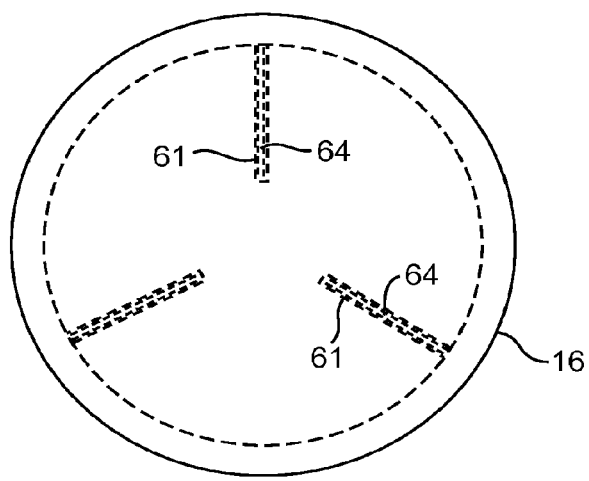
FIG. 5 shows a plan view of a core of a prosthetic disc, according to one embodiment of the present invention.

Referring to FIG. 5, the core 16 may be formed with narrow, angularly spaced, blind passages 61 which accommodate titanium pins 64. In many embodiments, the core 16 itself is transparent to X-radiation and so is invisible in a post-operative X-ray examination. The pins 64 serve as radiographic markers and enable the position of the core 16 to be ascertained during such examination.

Figure 2:
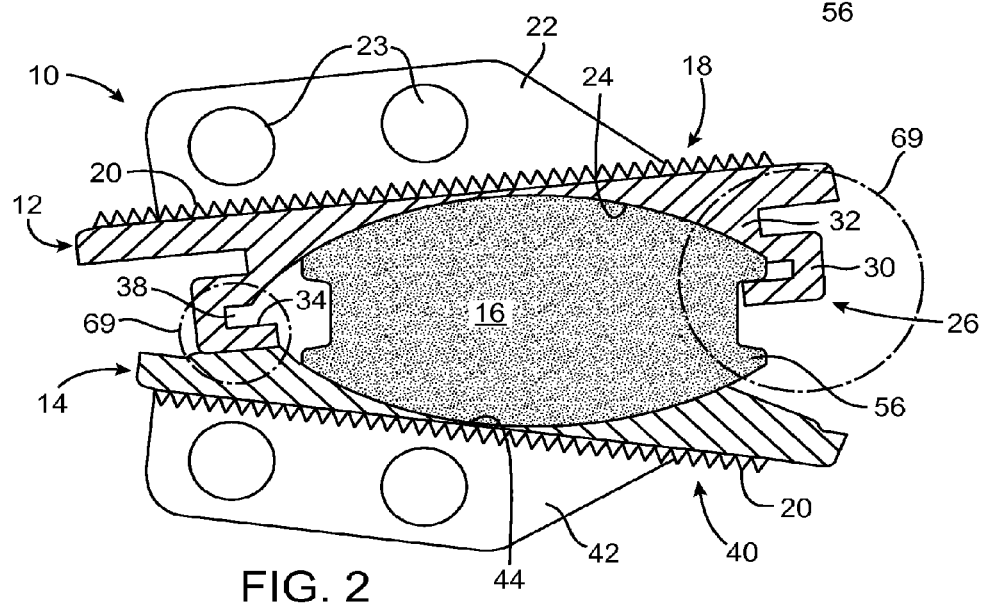
FIG. 2 shows a side view of the prosthetic disc in FIG. 1 after sliding movement of the plates over the core.

In the assembled disc 10, the complementary and cooperating spherical surfaces of the plates and core allow the plates to slide or articulate over the core through a fairly large range of angles and in all directions or degrees of freedom, including rotation about the central axis 62. FIGS. 1 and 4 show the disc 10 with the plates 12 and 14 and core 16 aligned vertically with one another on the axis 62. FIG. 2 illustrates a situation where maximum anterior flexion of the disc 10 has taken place. At this position, the upper rib 56 has entered the hollow 38 of the U-shaped member 30, the lower surface of the rib 56 has moved into contact with the upper surface 34 of the flange 28, the flange having moved into the groove 54, and the lower surface 36 of the flange has moved into contact with the upper surface of the ledge formation 46, as will be seen in the encircled areas 69. Abutment between the various surfaces prevents further anterior flexure. The design also allows for the inner extremity of the flange 28 to abut against the base of the groove 54, thereby limiting further relative movement between the core and plate. A similar configuration is achieved in the event of maximum posterior flexure of the plates 12, 14 over the core, such as during spinal extension and/or in the event of maximum lateral flexure.

Figure 3:
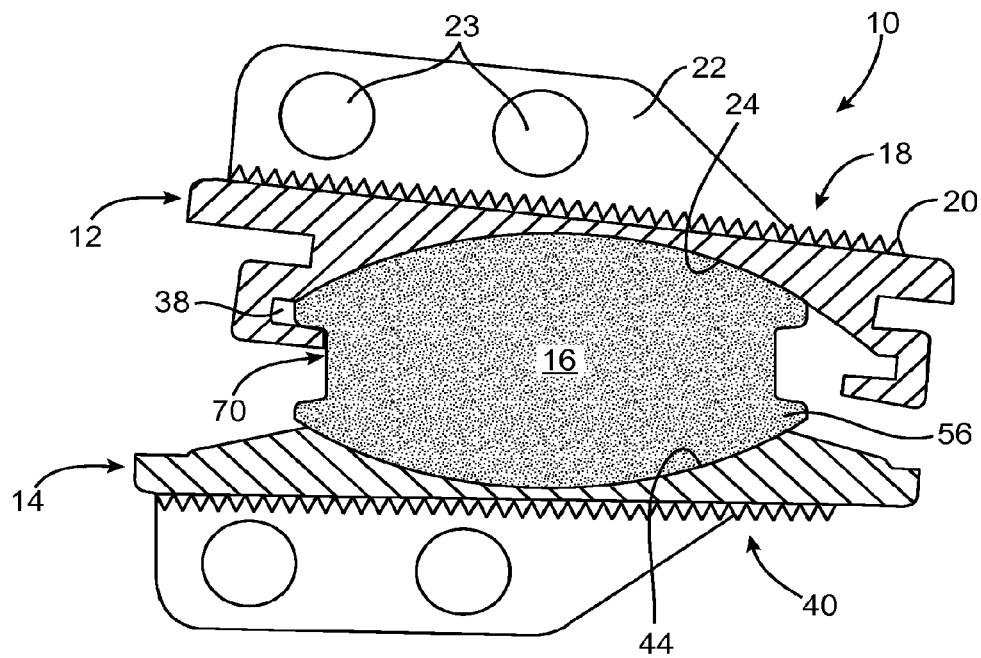
FIG. 3 shows a side view of the prosthetic disc in FIG. 1 after translational movement of the plates relative to the core.

FIG. 3 illustrates how the disc 10 can also allow for translational movement of the plates relative to the core. In the illustrated situation there has been lateral translation of the plates relative to the core. The limit of lateral translation is reached when the inner extremity of the flange 28 abuts the base of the groove 54 as indicated by the numeral 70.

The flange 28 and the groove 54 defined between the ribs 56, prevent separation of the core from the plates. In other words, the cooperation of the retaining formations ensures that the core is held captive between the plates at all times during flexure of the disc 10.

In an alternative embodiment, the continuous annular flange 28 may be replaced by a retaining formation comprising a number of flange segments which are spaced apart circumferentially. Such an embodiment could include a single, continuous groove 54 as in the illustrated embodiment. Alternatively, a corresponding number of groove-like recesses spaced apart around the periphery of the core could be used, with each flange segment opposing one of the recesses. In another embodiment, the continuous flange or the plurality of flange segments could be replaced by inwardly directed pegs or pins carried by the upper plate 12. This embodiment could include a single, continuous groove 54 or a series of circumferentially spaced recesses with each pin or peg opposing a recess.

In yet another embodiment, the retaining formation(s) could be carried by the lower plate 14 instead of the upper plate, i.e. the plates are reversed. In some embodiments, the upper (or lower) plate is formed with an inwardly facing groove, or circumferentially spaced groove segments, at the edge of its inner, curved surface, and the outer periphery of the core is formed with an outwardly facing flange or with circumferentially spaced flange segments.

Although the foregoing is a complete and accurate description of the invention, any of a number of modifications, additions or the like may be made to the various embodiments without departing from the scope of the invention. Therefore, nothing described above should be interpreted as limiting the scope of the invention at it is described in the claims.

What is claimed is:

1. A prosthetic disc for insertion between adjacent vertebrae, the prosthetic disc comprising:
   a first plate having a first surface configured to engage a vertebra and an opposite inwardly directed bearing surface;
   a second plate having a second surface configured to engage a vertebra and an opposite inwardly directed bearing surface;
   a rigid mobile core having first and second bearing surfaces configured to cooperate with the bearing surfaces of the first and second plates to allow the first and second plates to slide and translate over the core and a lateral edge between the first and second bearing surfaces; and
   a retaining formation which holds the core captive between the first and second plates;
   wherein the retaining formation includes two or more recesses circumferentially spaced apart about the periphery of the core and two or more inwardly directed pegs on the first plate each peg opposing a circumferentially spaced recess;
   wherein the circumferentially spaced recesses extend in a direction radially inward from the lateral edge of the core toward a center portion of the core.

2. A prosthetic disc as in claim 1, wherein at least one of the first and second bearing surfaces of the core is spherical.

3. A prosthetic disc as in claim 2, wherein at least one of the bearing surfaces of the first and second plates is a concave spherical surface which matches a curvature of the spherical surface of the core.

4. A prosthetic disc as in claim 2, wherein both of the first and second bearing surfaces of the core are spherical.

5. A prosthetic disc as in claim 1, wherein the retaining formation defines a stop structure to limit relative inclination of the plates during sliding movement of the plates over the core.

6. A prosthetic disc as in claim 1, wherein the retaining formation allows anterior, posterior and lateral motion of the core with respect to the first and second plates.

7. A prosthetic disc as in claim 1, wherein the core has a substantially circular perimeter.

8. A prosthetic disc as in claim 1, wherein each peg extends into a recesses.

9. A prosthetic disc as in claim 1, wherein the core is symmetrical about a central, equatorial plane which bisects the core laterally.

10. A prosthetic disc as in claim 1, wherein the lateral edge is a continuous annular lateral edge.

* * * * *